United States Patent [19]

Coffey et al.

[11] Patent Number: 4,823,042

[45] Date of Patent: Apr. 18, 1989

[54] SONIC TRANSDUCER AND METHOD FOR MAKING THE SAME

[75] Inventors: Kenneth W. Coffey, Tulsa; Toby E. Smith, Broken Arrow, both of Okla.

[73] Assignee: Rich-Mar Corporation, Tulsa, Okla.

[21] Appl. No.: 180,602

[22] Filed: Apr. 5, 1988

Related U.S. Application Data

[63] Continuation-in-part of Ser. No. 886,826, Jul. 18, 1986, abandoned.

[51] Int. Cl.⁴ .............................................. H01L 41/08
[52] U.S. Cl. ..................................... 310/322; 310/312; 310/324; 310/334
[58] Field of Search ......... 310/312, 322, 324, 334–337

[56] References Cited

U.S. PATENT DOCUMENTS 3,578,995  5/1971  Massa .............................. 310/324 X
3,943,388  3/1976  Massa .............................. 310/324 X
4,437,032  3/1984  Gelhard .............................. 310/324

OTHER PUBLICATIONS

NASA Technical Support Package on Broadband Ultrasonic Transducers for Mar./Apr. 1986, NASA Tech. Brief, vol. 10, No. 2, Item #50, FIG. 3(a), p. 1.

Primary Examiner—Mark O. Budd
Attorney, Agent, or Firm—Laney, Dougherty, Hessin & Beavers

[57] ABSTRACT

Sonic transducer and method for making the same. A sonic transducer of the type used in generating ultrasound frequencies for medical therapy includes a substantially planar circular piezoelectric crystal which is bonded to the rear surface of a circular metal diaphragm. The diaphragm front surface includes a substantially planar applicating face and an annular non-parallel surface surrounding the applicating face. The transducer may be excited to produce maximum ultrasound energy over a relatively broad frequency range.

3 Claims, 3 Drawing Sheets

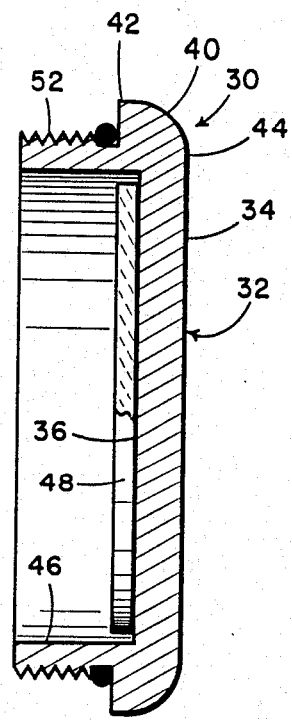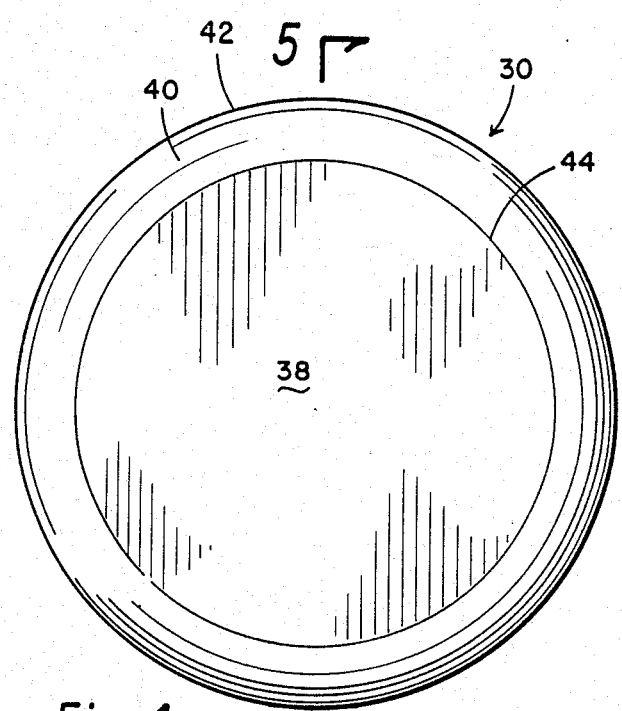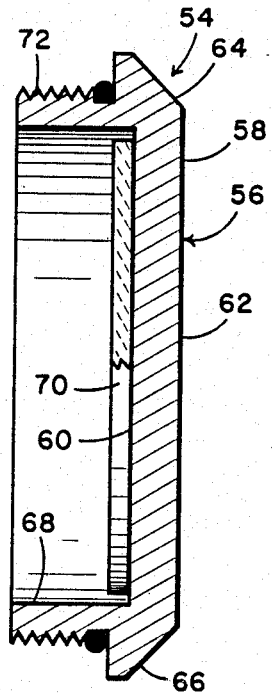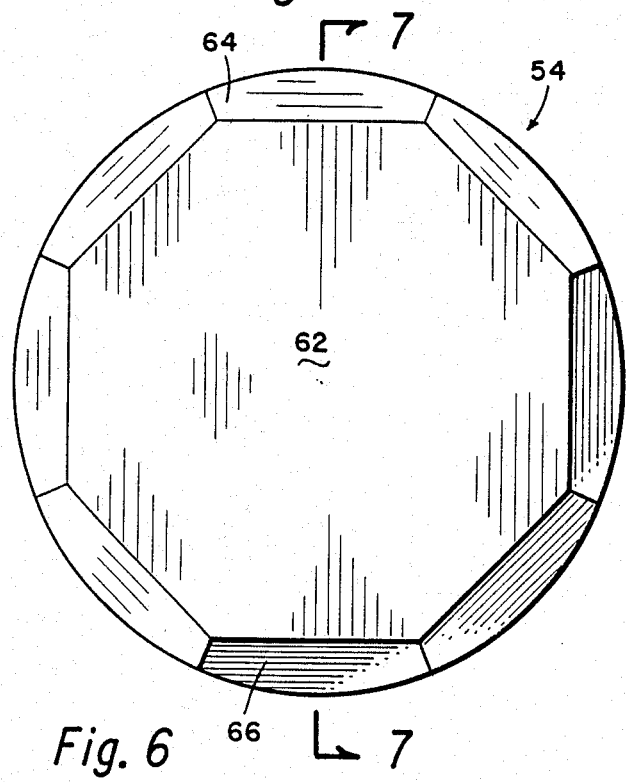

SONIC TRANSDUCER AND METHOD FOR MAKING THE SAME

This is a continuation-in-part of co-pending application Ser. No. 886,826 filed on July 18, 1986, now abandoned.

BACKGROUND OF THE INVENTION

1. Field of the Invention

This invention relates to sonic transducers and more particularly to such transducers which include a piezoelectric crystal which is bonded to a diaphram.

2. Description of the Prior Art

The term "sonic transducer" as used herein refers to a device which may be mechanically deformed by application of an electrical signal thereto. The term also includes a device which generates an electrical signal in response to mechanical deformation. When a periodic voltage is applied to a sonic transducer, mechanical compression waves are generated therein which produce a standing wave pattern in the device. A sonic transducer is typically designed to operate at a selected frequency. It should be appreciated that the term as used herein includes devices which operate as described regardless of the operating frequency.

One application for a sonic transducer is as an ultrasound therapy device in the medical field. In such an application, a periodic voltage is applied to the sonic transducer which is placed against the skin of a patient undergoing treatment. Ultrasonic energy generated by the transducer heats up the tissue beneath the skin thereby producing beneficial therapeutic effects.

A sonic transducer or applicator in an ultrasound therapy device sometimes includes a substantially planar diaphram which is typically made of metal. A substantially planar piezoelectric crystal is bonded to the rear surface of the applicator which in turn is mounted on a handle held by an operator of the ultrasound therapy device during treatment. The handle is connected by an electrical cable to a periodic voltage source which is applied through the handle to the crystal. When the voltage source is energized, the crystal vibrates thus generating vibrations in the applicator which may be placed against the skin of a patient.

A piezoelectric crystal has only a very narrow range of frequencies in which it can vibrate with optimum deflection. Each crystal typically has a minimum impedance (known as the point of resonance) which occurs within one narrow frequency range and a maximum impedance (known as the point of anti-resonance) which occurs within a second narrow frequency range. The circuit may be designed to apply voltage either within the first range or the second range in order to optimize deflection.

When the crystal is vibrated in its optimum frequency range, crystal deformation is at a maximum and thus ultrasonic energy generated by the device is maximumized. Although the crystal may vibrate outside of this range, crystal deformation is substantially reduced thereby reducing the ultrasonic energy generated.

Sophisticated electronic circuitry has been developed to automatically tune the frequency of the voltage source to the point of resonance or anti-resonance, depending upon the circuitry configuration. A problem which exists with this scheme, with either automatic or manual tuning, relates to the fact that man-made crystals typically have a number of small impedance peaks and valleys as the frequency of the voltage applied to the crystal varies. Thus, it may be possible to unknowingly tune the voltage source to a frequency which is centered about one of the many small peaks or valleys which does not represent the absolute maximum, or minimum if tuning to the point of resonance, impedance.

In order to overcome the above-enumerated problems it would be desirable to produce a crystal which has a relatively broad range of frequencies in which it could be vibrated while generating maximum crystal deformation. It is known in the prior art that modifying the surface of a crystal to produce a substantially planar surface on one side and a substantially concave surface on an opposing side produces a crystal which operates at substantially its maximum energy output over a relatively broad range of frequencies. Since shaping crystals is a complicated and expensive process, this approach has not been universally accepted.

SUMMARY OF THE INVENTION

The method of the instant invention comprises bonding a piezoelectric crystal to the rear surface of a substantially planar diaphram. The front surface of the diaphram is shaped until a substantial portion thereof is substantially non-parallel to the rear surface.

A sonic transducer constructed in accordance with the instant invention has a relatively broad range of frequencies in which the transducer vibrates at maximum energy responsive to electrical stimulation and in which generation of electrical signals in the transducer is maximized responsive to mechanical deformation.

A sonic transducer constructed in accordance with the instant invention also has a lower mechanical impedance than prior art transducers and thus provides more efficient conversion of electrical to mechanical energy than prior art transducers.

These and other advantages will become more fully apparent when the following detailed description is read in view of the accompanying drawings wherein:

FIG. 4 is a view of a first embodiment of a sonic transducer made in accordance with the instant invention.

FIG. 5 is a view taken along line 5—5 in FIG. 4.

FIG. 6 is a view of the front surface of a second embodiment of a sonic transducer made in accordance with the instant invention.

FIG. 7 is a view taken along line 7—7 in FIG. 6.

DETAILED DESCRIPTION OF THE PREFERRED EMBODIMENTS OF THE INSTANT INVENTION

Figure 1:
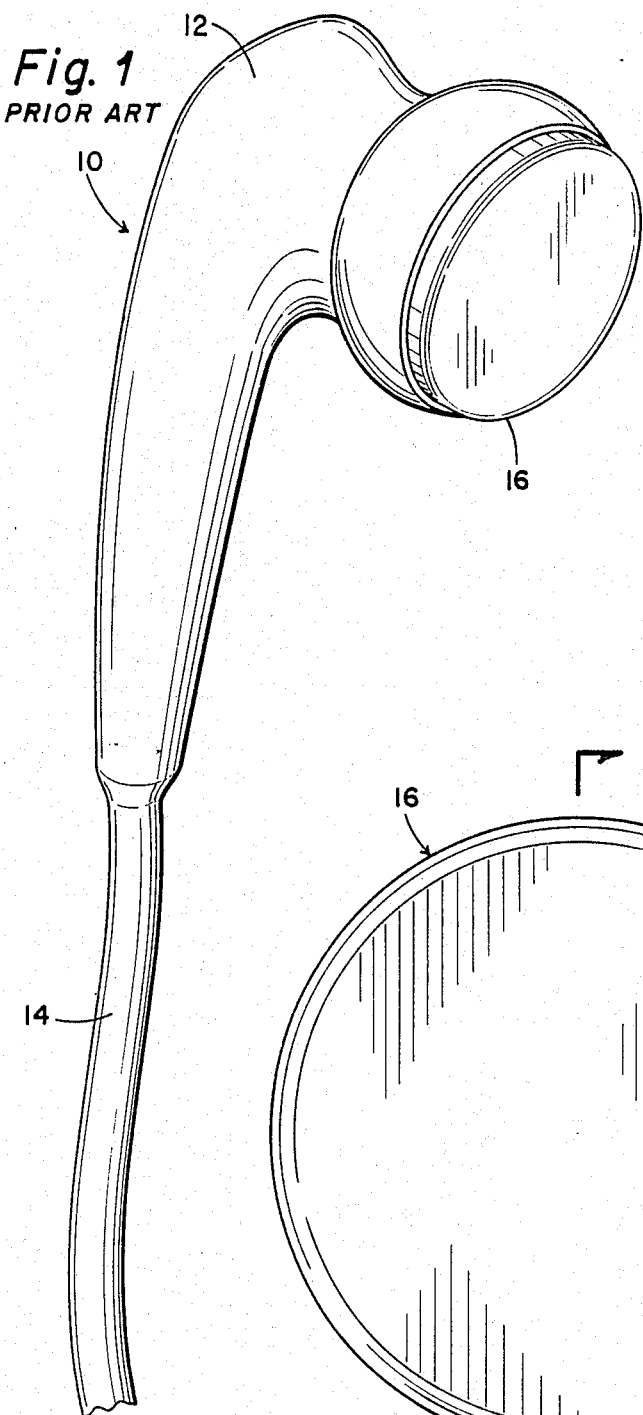
FIG. 1 is a perspective view of the handle of a prior art ultrasound therapy device having an applicator mounted thereon.

Turning now to the drawings, and particularly to FIG. 1, indicated generally at 10 is a portion of a conventional ultrasound therapy device. Included therein is a handle 12 which is connected to an electrical cable 14. Cable 14 is connected to a conventional periodic voltage source which may be tuned to generate periodic voltages of varying frequencies. Mounted on handle 12 is a metal applicator 16.

The applicator includes a front surface 18 and a rear surface 20. Rear surface 20 comprises the end of a bore 22 which is formed in the applicator. The radially outer surface of the applicator comprises a smooth cylindrical portion 24 and a threaded portion 26. A rounded corner 28 connects the surface of cylindrical portion 24 with front surface 18. An o-ring 31 seals bore 22 and the interior of handle 12 from the surrounding atmosphere when applicator 16 is threadably engaged with female threads (not visible) in handle 12 as shown in the view of FIG. 1.

A round, substantially planar piezoelectric crystal 29 is mounted on rear surface 20 of the applicator. The crystal is electrically bonded to applicator 16. When the applicator is threadably mounted on handle 12 as shown in FIG. 1, an electrode inside the handle (not visible) is firmly urged against crystal 29. Periodic voltage is applied to crystal 29 by placing one side of the voltage generator output on the female threads which receive threads 26 and the other side of the output on the electrode which is urged against the crystal. The periodic voltage source may therefore be applied across the longitudinal axis of the crystal.

Turning now to FIGS. 4 and 5, indicated generally at 30 is a sonic transducer constructed in accordance with the method and apparatus of the instant invention. Included therein is a metal applicator 32. The applicator includes a front surface 34 and a rear surface 36. Included in the front surface is a substantially planar applicating face 38. The applicating face is bounded by a non-parallel annular portion 40 of front surface 34. Non-parallel portion 40 is received between a circular outer boundry 42, which is defined by the radially outer circumference of the applicator, and a circular inner boundry 44, which is the radially outer circumference of applicating face 38. As shown in the drawings, applicating face 38 and non-parallel portion 40 are substantially coaxial. In the embodiment of FIGS. 4 and 5, non-parallel portion 40 comprises approximately 25% of the projected surface area of front surface 34.

As shown in FIG. 5, non-parallel portion 40, in cross-section, comprises an arc between boundries 42, 44.

Figure 3:
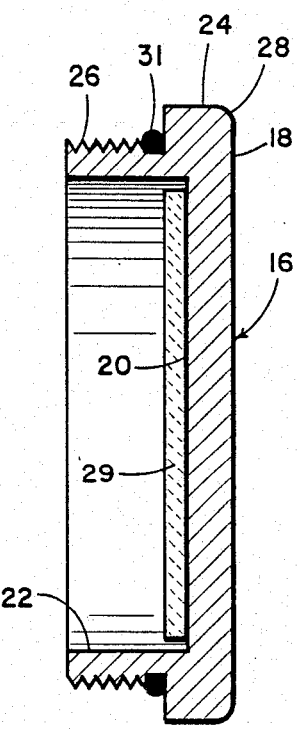
FIG. 3 is a cross-sectional view taken along lines 3—3 in FIG. 2.
Figure 2:
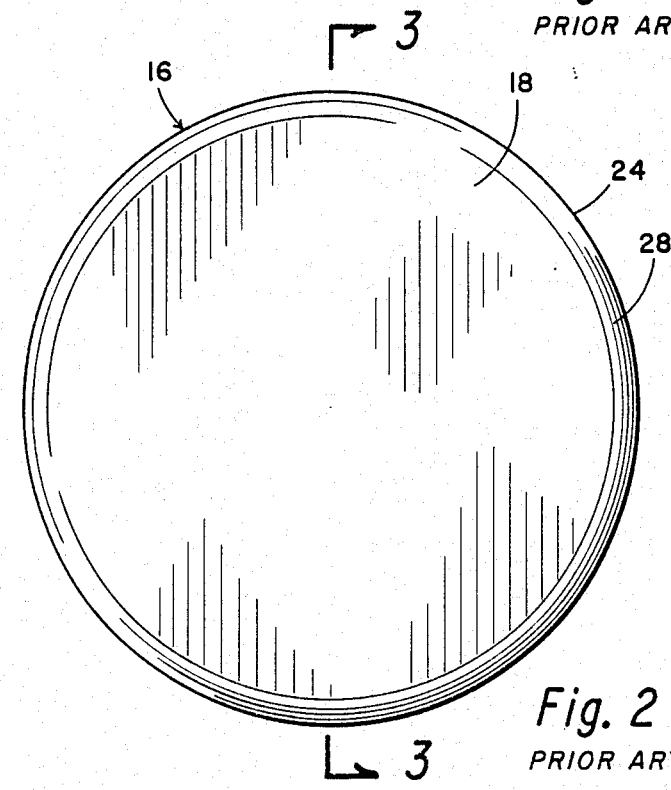
FIG. 2 is a view of the front surface of the applicator shown in FIG. 1.

As in the prior art applicator shown in FIGS. 1-3, applicator 32 includes therein a bore 46 with a piezoelectric crystal 48 being bonded to rear surface 36 of the applicator. Crystal 48 is substantially identical to crystal 29. Radially outer threads 52 are formed on applicator 32 to provide means for mounting the applicator on handle 12 in the same fashion that applicator 16, in FIGS. 2 and 3, is mounted on the handle in FIG. 1. In the same manner as described for the prior art device in FIGS. 1-3, a periodic voltage source may be applied between an electrode in handle 12, which is urged against the rear surface of crystal 48 when applicator 32 is mounted on the handle, and the applicator itself thereby placing the voltage across the longitudinal axis of the crystal.

Examining now FIGS. 6 and 7, shown therein is a sonic transducer 54 constructed in accordance with the method and apparatus of the instant invention. Included therein is a metal applicator 56 having a front surface 58 and a rear surface 60. Front surface 58 includes therein a substantially planar applicating face 62. The outer perimeter of the applicating face is bounded by a plurality of substantially planar surfaces, two of which are surfaces 64, 66, which define a non-parallel portion of front surface 58 adjacent the circumference of the front surface. Each of the formed surfaces, like surfaces 64, 66, are at an angle of substantially 135° to applicating face 62.

Like the embodiment of FIGS. 4 and 5, applicator 56 includes therein a bore 68 having a crystal 70, which is substantially identical to crystals 29, 48, mounted on the end thereof. Threads 72 are provided for mounting the applicator on handle 12 and a periodic voltage may be applied to crystal 70 in the same manner as voltage is applied to crystal 48.

Figure 8:
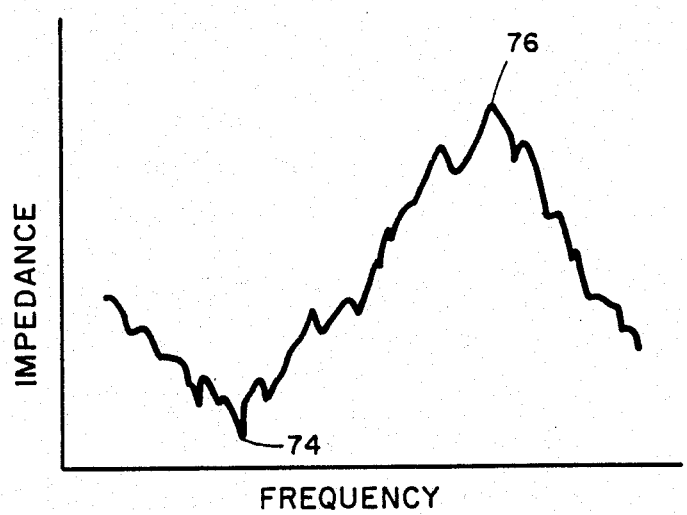
FIG. 8 is a chart showing the impedance of the prior art sonic transducer of FIGS. 1-3 as a function of frequency.
Figure 9:
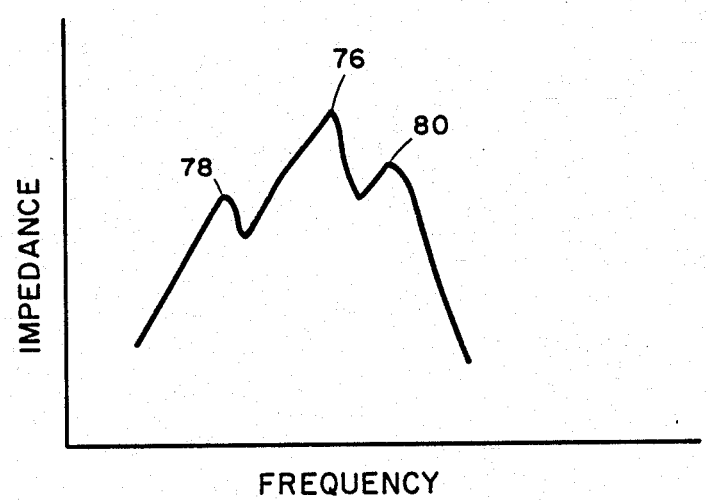
FIG. 9 is an expanded-scale chart of a portion of the chart of FIG. 8.

Considering now the operation of the prior art device shown in FIGS. 1-3, attention is directed to FIGS. 8 and 9. FIG. 8 is a graph of the impedance of crystal 29, when mounted on applicator 16, as the frequency of the periodic voltage applied to the crystal is varied. It can be seen that there is a minimum impedance at point 74 and a maximum impedance at point 76. The curve for crystal 29 is a typical one for manmade crystals. Such crystals have a minimum impedance (point 74), known as the point of resonance, and a maximum impedance (point 76), known as the point of anti-resonance. Depending upon the configuration of the periodic voltage source, it is desirable to drive a crystal either at its point of resonance or at its point of anti-resonance in order to generate maximum crystal deflection and thereby maximize the ultrasonic energy.

Assume that the periodic voltage generator (not shown) connected to cable 14 in FIG. 1 is designed to drive the crystal at its point of anti-resonance. FIG. 9 is an enlarged view of a portion of the curve of FIG. 8 about point 76. It can be seen in FIG. 9 that false peaks 78, 80 are adjacent point 76. Indeed, such peaks and valleys occur throughout the curve of FIG. 8 and are characteristic of the frequency response of man-made crystals.

When tuning the periodic voltage generator of the prior art device shown in FIG. 1, the aim is to select the frequency which resonates the crystal at its point of anti-resonance. Whether tuning is accomplished manually or by automatic tuning circuitry, it is possible to tune one of the false peaks, like peaks 78, 80, because it will be viewed as generating a maximum in the ultrasonic energy output in the frequencies around the false peak.

Figure 10:
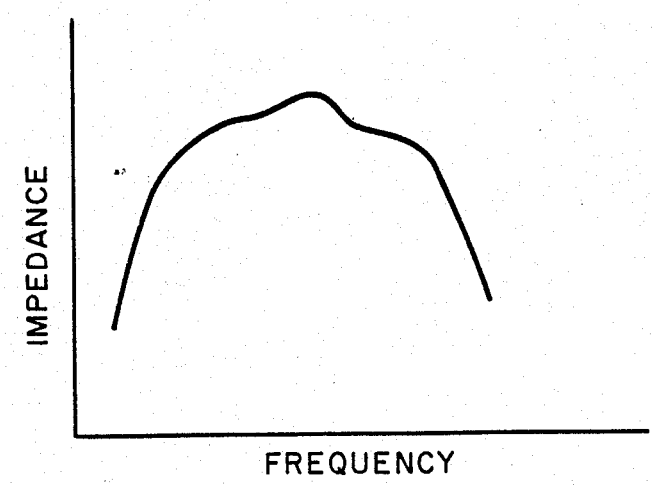
FIG. 10 is a chart on the same scale as the chart of FIG. 9 showing the impedance of the sonic transducer of the invention as a function of frequency.

Considering now the operation of the embodiments of FIGS. 4 and 5 and 6 and 7, attention is directed to FIG. 10.

FIG. 10 is a view on the same scale as the chart in FIG. 9 but shows the frequency response of crystal 48 around the point of anti-resonance when the crystal is in the configuration shown in FIGS. 4 and 5. As can be seen, the curve is considerably flattened thus eliminating the need for tuning over a narrow range and preventing tuning to one of the false peaks. With the curve as shown in FIG. 10, sonic transducer 30 generates maximum ultrasound energy over a broad range of frequencies when compared to the prior art device of FIGS. 1–3.

Crystal 70, in sonic transducer 54, generates a curve similar to that of FIG. 10 with the crystal in the configuration shown in FIGS. 6 and 7 and thus provides the same advantages as the embodiment of FIGS. 4 and 5.

It should be appreciated that additions and modifications may be made to the instant embodiments of the invention without departing from the spirit thereof which is defined in the following claims.

We claim:

1. A sonic transducer, comprising:
   a piezoelectric crystal having a response to an applied signal, said response including a minimum impedance peak at a resonance frequency, a maximum impedance peak at an anti-resonance frequency, and intermediate impedance peaks near said minimum and maximum impedance peaks at frequencies near said resonance and anti-resonance frequencies;
   a substantially tubular wall portion having a radially inner surface; and
   means, connected to said wall portion and said crystal, for producing, in response to a signal applied to said crystal, an output having a substantially flat minimum impedance characteristic throughout a range of frequencies about said resonance frequency of said crystal and a substantially flat maximum impedance characteristic throughout a range of frequencies about said anti-resonance frequency of said crystal so that said output does not have said intermediate impedance peaks characteristic of said crystal, said means including an applicator body portion comprising:
   a planar circular rear surface extending to said radially inner surface across an end of said wall portion, said planar circular rear surface having said crystal connected thereto, said crystal extending substantially to said radially inner surface of said wall portion; and
   a front surface overlying said planar circular rear surface, said front surface having a projected area and said front surface including:
   a planar circular face disposed a distance from said rear surface and parallel thereto, said planar circular face having substantially the same surface area as said crystal; and
   a substantially annular edge surface extending only radially outwardly and rearwardly from said planar circular face and in substantially non-parallel relationship to said rear surface, said substantially annular edge surface comprising approximately 25% of said projected area of said front surface.

2. A sonic transducer, comprising:
   a piezoelectric crystal having a response to an applied signal, said response including a minimum impedance peak at a resonance frequency, a maximum impedance peak at an anti-resonance frequency, and intermediate impedance peaks near said minimum and maximum impedance peaks at frequencies near said resonance and anti-resonance frequencies;
   a substantially tubular wall portion having a radially inner surface; and
   means, connected to said wall portion and said crystal, for producing, in response to a signal applied to said crystal, an output having a substantially flat minimum impedance characteristic throughout a range of frequencies about said resonance frequency of said crystal and a substantially flat maximum impedance characteristic throughout a range of frequencies about said anti-resonance frequency of said crystal so that said output does not have said intermediate impedance peaks characteristic of said crystal, said means including an applicator body portion comprising:
   a planar circular rear surface extending to said radially inner surface across an end of said wall portion, said planar circular rear surface having said crystal connected thereto, said crystal extending substantially to said radially inner surface of said wall portion; and
   a front surface overlying said planar circular rear surface, said front surface having a projected area and said front surface including:
   a planar face disposed a distance from said rear surface and parallel thereto, said planar face having substantially the same surface area as said crystal; and
   a substantially annular edge surface extending only radially outwardly and rearwardly from said planar face and in substantially non-parallel relationship to said rear surface, said substantially annular edge surface comprising a plurality of substantially planar surfaces adjoining each other in end-to-end fashion around the periphery of said planar face.

3. A transducer as defined in claim 2, wherein:
   said planar face of said front surface has an octagonal shape; and
   said plurality of substantially planar surfaces is characterized by eight beveled edges, each of said edges extending at an angle of substantially 135° from a respective edge of said octagonally shaped planar face.

* * * * *